United States Patent [19]

Strickland

[11] Patent Number: 4,995,874

[45] Date of Patent: Feb. 26, 1991

[54] DISPOSABLE SYRINGE DEVICE

[76] Inventor: H. Allen Strickland, 83 Beach St., Westerly, R.I. 02891

[21] Appl. No.: 370,718

[22] Filed: Jun. 23, 1989

[51] Int. Cl.⁵ .............................................. A61M 5/32
[52] U.S. Cl. .................................... 604/195; 604/110
[58] Field of Search ............... 604/195, 110, 187, 218, 604/263, 220

[56] References Cited

U.S. PATENT DOCUMENTS

| | | | |
|---|---|---|---|
| 4,675,005 | 6/1987 | DeLuccia | 604/195 |
| 4,747,830 | 5/1988 | Gloyer et al. | 604/110 |
| 4,790,822 | 12/1988 | Haining | 604/195 |

Primary Examiner—John D. Yasko

Attorney, Agent, or Firm—Nies, Kurz, Bergert & Tamburro

[57] ABSTRACT

A disposable syringe having a needle which may be easily withdrawn to safety after use is disclosed. The syringe includes a cylinder and plunger in which a threaded extension or threadlock on the forward end of the plunger is capable of engaging a threadbore element positioned within the forward neck portion of the cylinder after the injectable fluid has been expelled from the cylinder. The threadbore element is secured to the needle. Rotation of the plunger causes the threadlock to engage the threadbore and the needle may be withdrawn into the interior of the cylinder by pulling the plunger rearwardly.

6 Claims, 2 Drawing Sheets

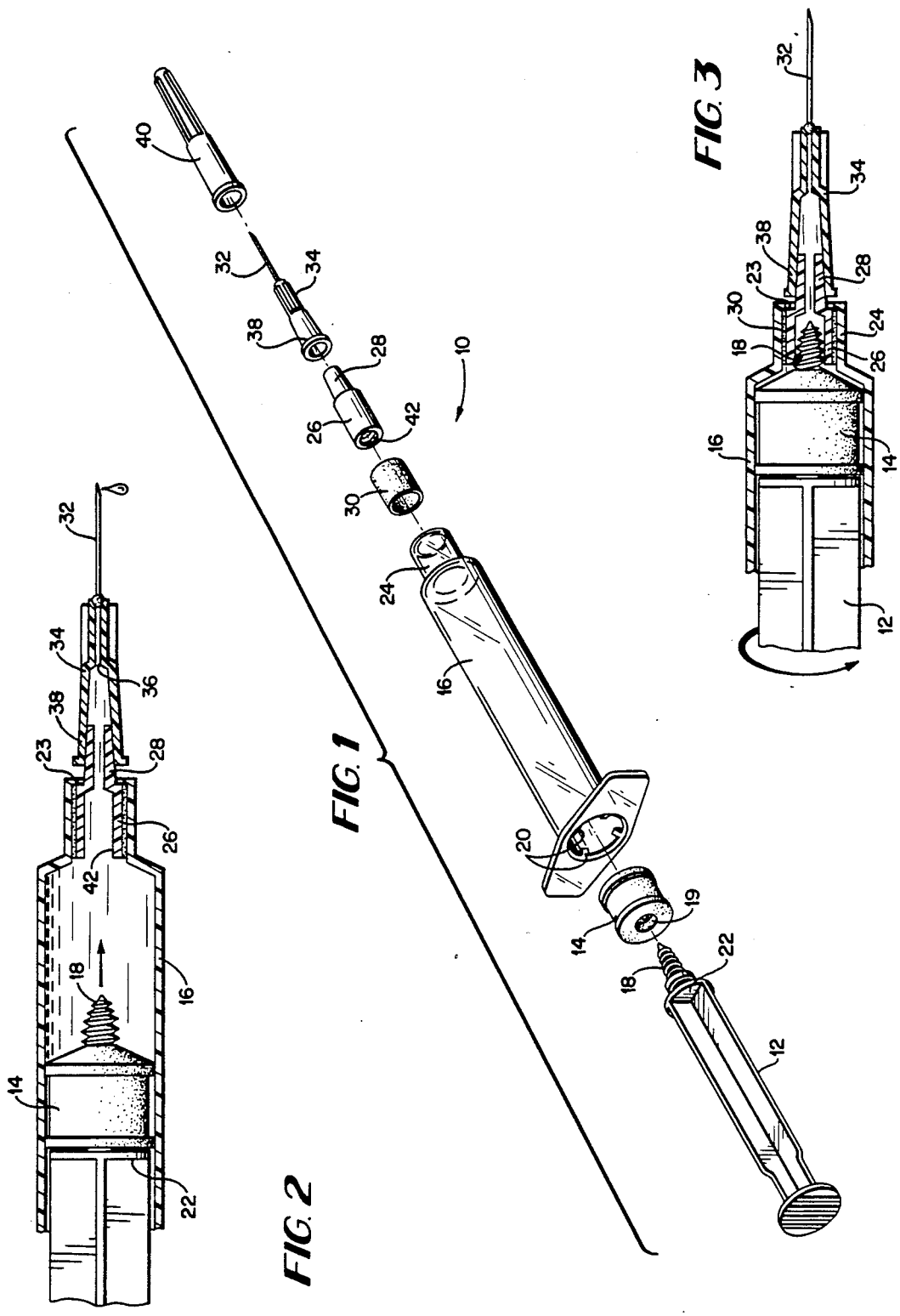

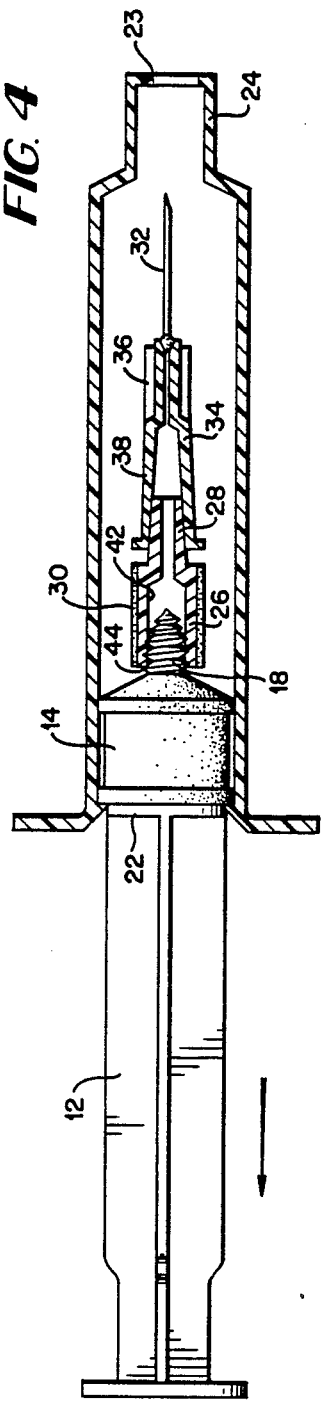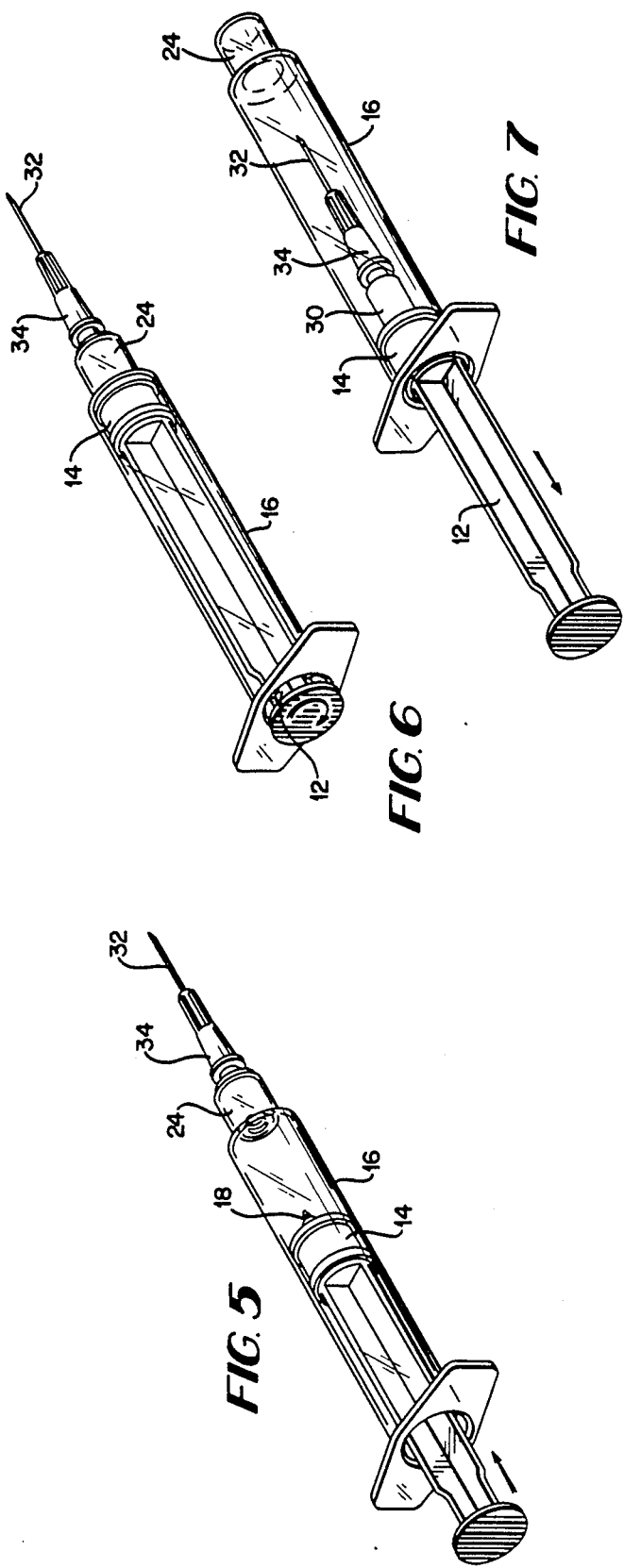

DISPOSABLE SYRINGE DEVICE

BACKGROUND AND SUMMARY OF THE INVENTION

The present invention relates to a disposable syringe device having a retractable needle or cannula. More particularly, the present invention relates to a disposable syringe which allows the needle to be retracted, once it has been used, to a position of safety so as to prevent personal contact with the needle tip.

The viral disease AIDS has become of great concern to health professionals because of its obvious potentially devastating impact on the health and monetary resources of this country. To date, the only "cure" which amounts to control, is through prevention of the spread of this uniformly fatal disease. The newest high-risk group is health care professionals.

Not only do known AIDS patients represent a source for the spread of disease among health care workers but so does the general population. There are large groups of people who have been exposed as intravenous drug users, people who have received blood transfusions during a certain period of time when there was no testing, and people who have been infected with the virus through sexual contact.

Health care workers, in addition, may be exposed within the hospital environment by contact with body secretions but, in particular, through accidental needle punctures.

Commercially available disposable syringes have certain generic characteristics and components which are used industry-wide. Indeed, many of these parts are interchangeable from manufacturer to manufacturer.

Previous syringe devices are described in the following U.S. patents: U.S. Pat. No. 4,026,287 to Haller; U.S. Pat. No. 4,507,117 to Vining et al.; U.S. Pat. No. 4,650,468 to Jennings; U.S. Pat. No. 4,675,005 to De-Luccia; U.S. Pat. No. 4,710,170 to Haber et al.; U.S. Pat. No. 4,747,830 to Gloyer et al.; U.S. Pat. No. 4,770,655 to Haber et al.; U.S. Pat. No. 4,790,822 to Haining; U.S. Pat. No. 4,801,295 to Spencer; U.S. Pat. No. 4,804,370 to Haber et al.; and U.S. Pat. No. 4,808,169 to Haber et al.

By the present invention, there is provided an improved syringe having a unique mechanism which allows the exposed needle after use to be easily withdrawn to safety within the syringe without the need for breakage of any portion of the device. Use of the syringe of the present invention virtually eliminates the potential for the health care worker to be stuck by an infected needle.

The present syringe has a threaded extension or threadlock at the forward end of the plunger which replaces the strut of the generic model. The threadlock passes through a fluid-tight threadport extending axially through the center of the rubber piston. In the post injection state the plunger threadlock has entered a threadbore element which is secured to the needle. The threadlock and threadbore may be easily engaged by a simple clockwise turn of the plunger. Upon engagement of the threadlock with the threadbore, the entire threadbore assembly, including gasket, hub and ultimately the needle, may be withdrawn safely into the syringe cylinder. At the base of the syringe cylinder, stop elements are positioned to prevent the plunger assembly from being removed from the back side of the syringe, further protecting the operator.

BRIEF DESCRIPTION OF THE DRAWINGS

FIG. 1 is an exploded perspective view of the syringe device of the present invention.

FIG. 2 is a cross sectional view of the syringe device of FIG. 1 showing the piston as positioned for movement axially within the cylinder.

FIG. 3 is a cross sectional view of the syringe device of FIG. 1 showing the threadlock of the plunger engaged with the threadbore.

FIG. 4 is cross sectional view of the syringe device of FIG. 1 showing the needle or cannula withdrawn within the cylinder.

FIGS. 5 through 7 are perspective views of the syringe device of FIG. 1 in various stages of operation.

DESCRIPTION OF THE PREFERRED EMBODIMENTS

In the embodiment of the invention as shown in FIGS. 1 through 7, there is provided a syringe device 10 in which a plunger 12 with removably attached piston 14 is positioned for axial movement within a cylinder or barrel 16. The cylinder 16 is generally of a clear plastic material for viewing of its contents. The plunger 12 is of a generally cruciform shape in cross section, with inner 22 and outer 23 end plates.

The piston 14 may be constructed of rubber or other resilient material. At the extreme inner end of the plunger 12 there is attached a tapered threadlock 18 as shown in FIG. 1 with the threadlock 18 having the capability of threadedly engaging a threadbore 42 as described hereinafter. The threadlock 18 is in the general form of the threaded portion of a screw and the piston 14 has an axial threadport 19 through which the threadlock 18 passes with a fluid tight fit, so that the forward end of the threadlock 18 extends beyond the piston 14 as shown in FIG. 2.

The cylinder 16 is provided at its outer end with a plurality of stops or ribs 20 which engage the inner end plate 22 of the plunger 12 upon rearward movement thereof to prevent complete withdrawal of the plunger 12 from the cylinder 16. As shown in FIGS. 1 and 4 through 7, the cruciform shaft of the plunger 12 is of reduced diameter at the rear end so as to clear the stops 20 during rotation. At the forward end of the cylinder 16 there is provided a neck portion 24 of reduced diameter which receives the threadbore element 26 with tapered hub portion 28 during the pre-injection stage, as shown in FIG. 2, and with a gasket member 30 being positioned between the threadbore 26 and the neck portion 24 to provide a fluid tight seal.

A cannula or hollow needle 32 is received in a tapered mounting post 34 having an axial passage 36 as shown in FIG. 4 and having an enlarged base portion 38 which fits in fluid tight engagement over the outer end of the hub 28. A tapered hollow sheath 40 may be removably fitted over the needle 32 and post 34.

The threadbore 26 is provided with an inner chamber or bore 42 extending the length of the threadbore 26 and hub portion 28. The bore 42 has threaded walls 44 adjacent the outer end of the hub 28 for engagement with the tapered threadlock 18. The hub 28 is tapered inwardly toward the forward end thereof and the inner bore 42 is of reduced diameter within the hub portion 28.

The gasket member 30 should fit securely around the circumference of the threadbore 26 so as to maintain its position on the threadbore 26 during axial movement and interaction with the neck portion 24 of the cylinder 16. The gasket 30 may be constructed of a resilient material such as moderately soft polyethylene or other similar material. In one embodiment, the gasket 30 had an outer diameter of 6 mm. and an inner diameter of 4 mm. Once stretched over the threadbore assembly, the combined outer diameter of the two components was 7 mm. The inner diameter of the cylinder neck 24 in this embodiment was also 7 mm. The outer surface of the gasket 30 is temporarily sealed to the inner surface of the cylinder neck 24 by capillary action during operation of the device.

As the threadlock 18 engages the threadbore 26, as shown in FIG. 3, the gasket 30 should have a sufficiently tight fit within the cylinder neck 24 to allow the threadlock 18 to press against and engage the threadbore 26 under normal manual pressure without having the gasket 30 pass forward through the neck 24. The forward edge 23 of the neck 24 may be rolled inwardly to produce a very slightly smaller diameter at the margin only, as shown in FIGS. 2 through 4, so as to prevent forward movement of the gasket 30. The fit of the gasket 30 within the neck 24 should then allow the threadbore 26 with attached gasket 30 to be withdrawn within the interior of the cylinder 16, as shown in FIG. 4. In this regard, the diameter of the post member 34 should be sufficiently small so as to pass rearwardly through the cylinder neck 24 to the position of FIG. 4.

In the use of the syringe device 10 of the present invention, the plunger 12 and cylinder 16 may be employed in the usual manner by moving the plunger 12 forward to expel an injectable fluid from the cylindrical chamber, as shown in FIGS. 2 and 5. Once the fluid has been expelled, the plunger 12 may be rotated by hand in a clockwise direction as shown in FIGS. 3 and 6 to cause the threadlock 18 to engage the threads 44 of threadbore 42. Generally about one half turn of the plunger 12 should be sufficient to cause the units to engage. After engagement of the threadlock 18 and threadbore 42, the outwardly extending portion, including hub member 28, gasket 30, post 34 and needle 32 may be withdrawn into the interior of the cylinder 16 by pulling the plunger 12 rearwardly as shown in FIGS. 4 and 7. In this latter position, the needle 32 is then safely stowed for disposal.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A disposable syringe device having a retractable needle, comprising:

a cylinder member having a neck portion at one end thereof; a plunger mounted for reciprocal movement within said cylinder, said plunger having a threaded portion at one end; a threadbore member mounted within said neck portion in fluid tight engagement therewith, said threadbore member having an inner bore with a threaded portion in said bore for receiving the threaded portion of said plunger; a tapered post member mounted on one end of said threadbore member outwardly of said cylinder, said post member having said needle mounted therein; and a gasket mounted about the circumference of said threadbore member to provide fluid tight engagement between the threadbore member and the neck portion of said cylinder.

2. The syringe device of claim 1 wherein said plunger has a piston member mounted on the threaded end portion of said plunger.

3. The syringe device of claim 1 wherein said threadbore member has a tapered hub portion on one end for receiving said post member.

4. The syringe device of claim 1 wherein said gasket is of a size and material so as to allow the threaded end portion of said plunger to press against and engage the threadbore upon forward movement of said plunger without having the gasket pass through the cylinder neck portion and wherein the threadbore member with attached gasket may be withdrawn through said cylinder neck upon rearward movement of said plunger.

5. The syringe device of claim 5 wherein the cylinder neck has a rolled forward edge producing a slightly smaller diameter at the extreme forward end of the cylinder neck to prevent forward movement of the gasket.

6. The syringe device of claim 2 wherein said threaded end portion of the plunger is of reduced diameter relative to the piston member.

* * * * *

UNITED STATES PATENT AND TRADEMARK OFFICE
CERTIFICATE OF CORRECTION

PATENT NO. : 4,995,874

DATED : February 26, 1991

INVENTOR(S) : H. Allen Strickland

It is certified that error appears in the above-identified patent and that said Letters Patent is hereby corrected as shown below:

Column 4, line 42, "claim 5" should read --claim 4--.

Signed and Sealed this

Twenty-first Day of July, 1992

Attest:

DOUGLAS B. COMER

*Attesting Officer*     *Acting Commissioner of Patents and Trademarks*